United States Patent [19]

Ichihashi et al.

[11] Patent Number: 5,184,157
[45] Date of Patent: Feb. 2, 1993

[54] OPHTHALMIC MEASUREMENT APPARATUS

[75] Inventors: Tadashi Ichihashi; Koichi Akiyama, both of Tokyo, Japan

[73] Assignee: Kowa Company Limited, Japan

[21] Appl. No.: 530,290

[22] Filed: May 30, 1990

[30] Foreign Application Priority Data

Jun. 29, 1989 [JP] Japan .................................. 1-165207

[51] Int. Cl.⁵ .............................................. A61B 3/10
[52] U.S. Cl. ...................................... 351/208; 351/221
[58] Field of Search ............... 351/205, 214, 221, 208; 128/633, 745; 606/4

[56] References Cited

U.S. PATENT DOCUMENTS 4,838,679 6/1989 Bille .................................. 351/221 X Primary Examiner—Rodney B. Bovernick
Attorney, Agent, or Firm—Bruce L. Adams; Van C. Wilks

[57] ABSTRACT

An ophthalmic measurement apparatus is provided in which a laser beam is converged at a selected point in a measurement zone within an eye and light scattered therefrom is photoelectrically detected via a measurement mask having an aperture of a prescribed size for ophthalmic measurement. During alignment the measurement zone is scanned at high speed by the laser beam with the same scanning width as the scanning width used during measurement. This makes it possible to observe any harmful light rays that will actually appear during measurement at those settings and to align the apparatus so that the harmful light rays do not come within the limiting aperture of the measurement mask, thereby enabling measurement to be conducted under optimum conditions.

15 Claims, 5 Drawing Sheets

OPHTHALMIC MEASUREMENT APPARATUS

BACKGROUND OF THE INVENTION

1. Field of the Invention

This invention relates to an ophthalmic measurement apparatus, and more particularly to an ophthalmic measurement apparatus which irradiates the interior of a patient's eye with a beam of laser light and uses the scattering of laser beam from the interior of the eye to output measurement quantities such as protein concentration in the anterior chamber of the eye.

2. Description of the Prior Art

Measurement of protein concentration in the anterior chamber of the eye is of considerable importance in determining whether the camera oculi is inflamed, that is, whether the blood-aqueous barrier function is normal or not. In one method that is frequently used for this a slit lamp microscope is employed to grade the concentration by observation with the naked eye, while in another method photographic techniques are used to obtain quantitative measurements. However, as yet there is no method that is easy to use clinically.

Data obtained with the conventional method of naked-eye measurement lacks reliability as judgments vary depending on the person making the measurement. One solution has been to use a method in which a beam of laser light is projected into the eye and the light scattering from the eye is detected and subjected to quantitative analysis.

Examples of such an ophthalmic measurement apparatus which irradiates the eye with a beam of laser light and detects the light scattered from the eye are disclosed in Japanese Patent Laying-open Nos. 120834/87 (corresponding to U.S. patent application Ser. No. 926,650 filed on Mar. 11, 1986) and 135128/88 (corresponding to U.S. Pat. No. 4,832,043). In such an arrangement, the beam from a laser light source is focused on a prescribed point in the eye such as in the anterior chamber, for example, and scattered light from the eye is detected, via a mask with a rectangular aperture of a prescribed size, by a photosensor which converts the light to an electrical signal which is processed to determine protein concentration or other such ophthalmic measurement quantities.

The extremely low intensity of the scattered laser light makes it susceptible to noise in the form of light other than light from the region of interest. Taking the detection of the anterior chamber as an example, if the measurement area is too close to the crystalline lens, light scattering from the crystalline lens will be picked up as noise which will affect the results.

To reduce or eliminate the effects of such noise, in the apparatus described in Japanese Patent Laid-open No. 135128/88 the laser beam is made to overscan the mask aperture and the difference is obtained between a signal obtained from the photosensor when the laser beam is within the limits of the aperture and a signal obtained when the beam is outside the aperture.

The human cornea has a strong lens effect which causes incident light that is not along the normal line to be refracted at the cornea surface. Hence, when the area on which the light impinges is changed the degree of refraction also changes, disturbing the relationship between the measurement area (point of laser beam convergence) and the mask of the light receiving section.

The depth of the aqueous humor in the anterior chamber is around 3 mm, thus the laser has to be focused on a median portion measuring 1 mm to 2 mm and the light scattered from this measurement area has to be accurately captured. This necessitates accurate alignment of the apparatus with the patient's eye, particularly in the horizontal plane, and a method of accurately achieving this alignment. Failure to align the system prior to carrying out measurements will result in the entry into the measurement mask aperture of various undesired light rays from areas other than the measurement area concerned, making it impossible to obtain accurate measurements.

SUMMARY OF THE INVENTION

An object of the present invention is therefore to provide an ophthalmic measurement apparatus which ensures accurate ophthalmic measurements by eliminating undesired light rays from areas other than the measurement area concerned.

In accordance with present invention, an ophthalmic measurement apparatus is provided in which a laser beam is projected at a selected point in a measurement zone within an eye to be examined and light scattered therefrom is photoelectrically detected for ophthalmic measurement. The apparatus includes a laser source for producing a laser beam. Means for projecting the laser beam to converge it to the point in the measurement zone are provided. A light receiving section is provided with a photosensor for photoelectrically detecting scattered laser light from the measurement zone via a measurement mask which has an aperture of a prescribed size and it is provided at a position that is conjugate with the point of convergence of the laser beam. Means for deflecting the laser beam in a prescribed direction for scanning the area of the measurement zone during alignment of the eye and during measurement; and means for processing signals received from the light receiving section to perform the ophthalmic measurement are provided. In accordance with the present invention the measurement zone is scanned during alignment at high speed by the laser beam which has the same scanning width as the scanning width used during measurement.

Thus, with the above arrangement, during alignment the laser beam performs high-speed scanning of the measurement zone at the same scanning width used for measurement scanning. Here, high-speed scanning signifies scanning of the measurement zone at a frequency such as 50 Hz or 60 Hz which is a high enough frequency to prevent a flicker effect when observed by the human eye. This high-speed laser beam scanning of the measurement zone during alignment at the same scanning width used for the measurement scanning makes it possible to observe any undesired light rays that actually appear during measurement at those settings. This therefore makes it possible to align the apparatus so that the undesired light rays do not come within the mask aperture, thereby enabling measurement to be conducted under optimum conditions. To accomplish this, the scanning width of the measurement zone by the laser beam is set so that it exceeds the width of the mask aperture.

Alignment of the apparatus may also be facilitated by using a configuration in which there is a conjugate relationship between the point of convergence of the laser beam and the measurement mask, and between the measurement mask and the alignment index. With such an arrangement, the examiner would be able to observe the alignment index as if it were at the point of laser beam convergence.

Thus, in accordance with this invention high-speed laser beam scanning of the measurement zone during alignment is effected at the same scanning width as that used for the measurement scanning, which makes it possible to observe any undesired light rays that will actually appear during the measurement. Moreover, forming an image of the alignment index makes it possible to observe directly the point of origin of scattered light that impinges on the photosensor, and therefore enables the apparatus to be aligned so that harmful light rays which are revealed by the high-speed scanning as coming from the cornea, crystalline lens or other such regions lying outside the zone of interest do not come within the area of the rectangular mask image. The effect of this is to increase the useful component of the measured signals and achieve a higher level of measurement precision.

BRIEF DESCRIPTION OF THE DRAWINGS

The purposes and features of the present invention will become more apparent from a consideration of the following detailed description taken in conjunction with the accompanying drawings in which.

DETAILED DESCRIPTION OF THE PREFERRED EMBODIMENTS

Figure 1:
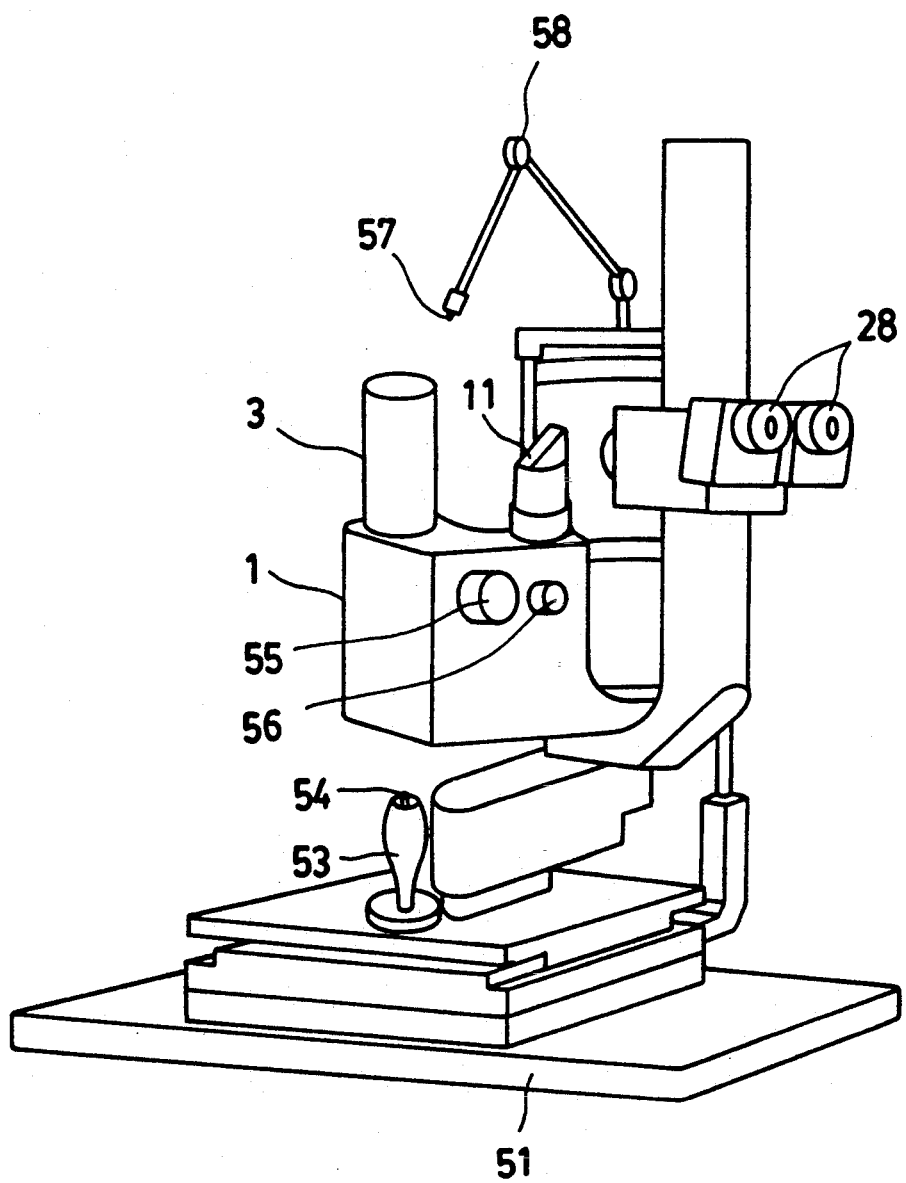
FIG. 1 is a perspective view of the ophthalmic measurement apparatus of the present invention.

The invention will now be described in detail on the basis of the preferred embodiments illustrated in the drawings.

Figure 2:
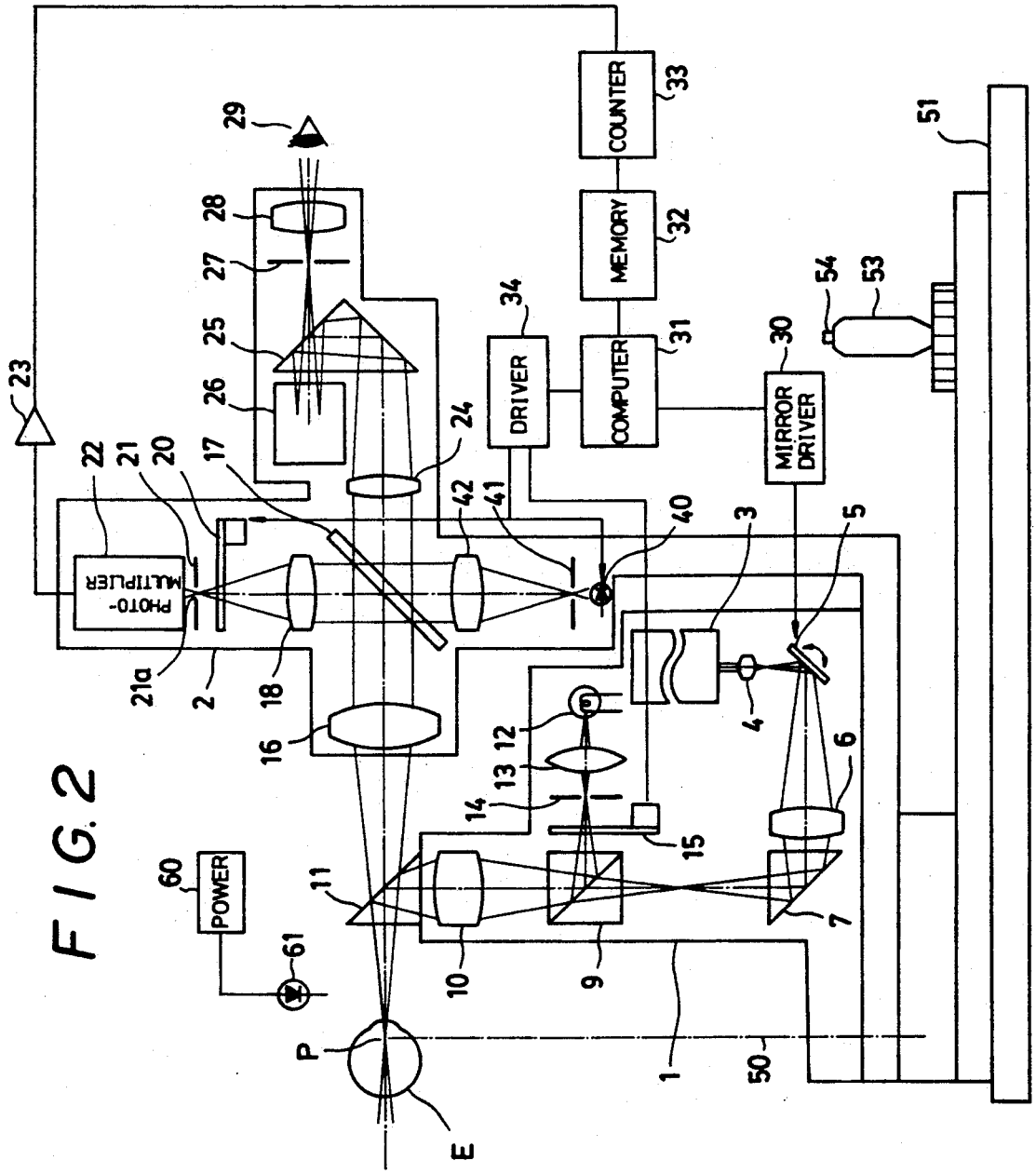
FIG. 2 is a schematic view of the internal configuration of the projection section of the apparatus shown in FIG. 1.
Figure 3:
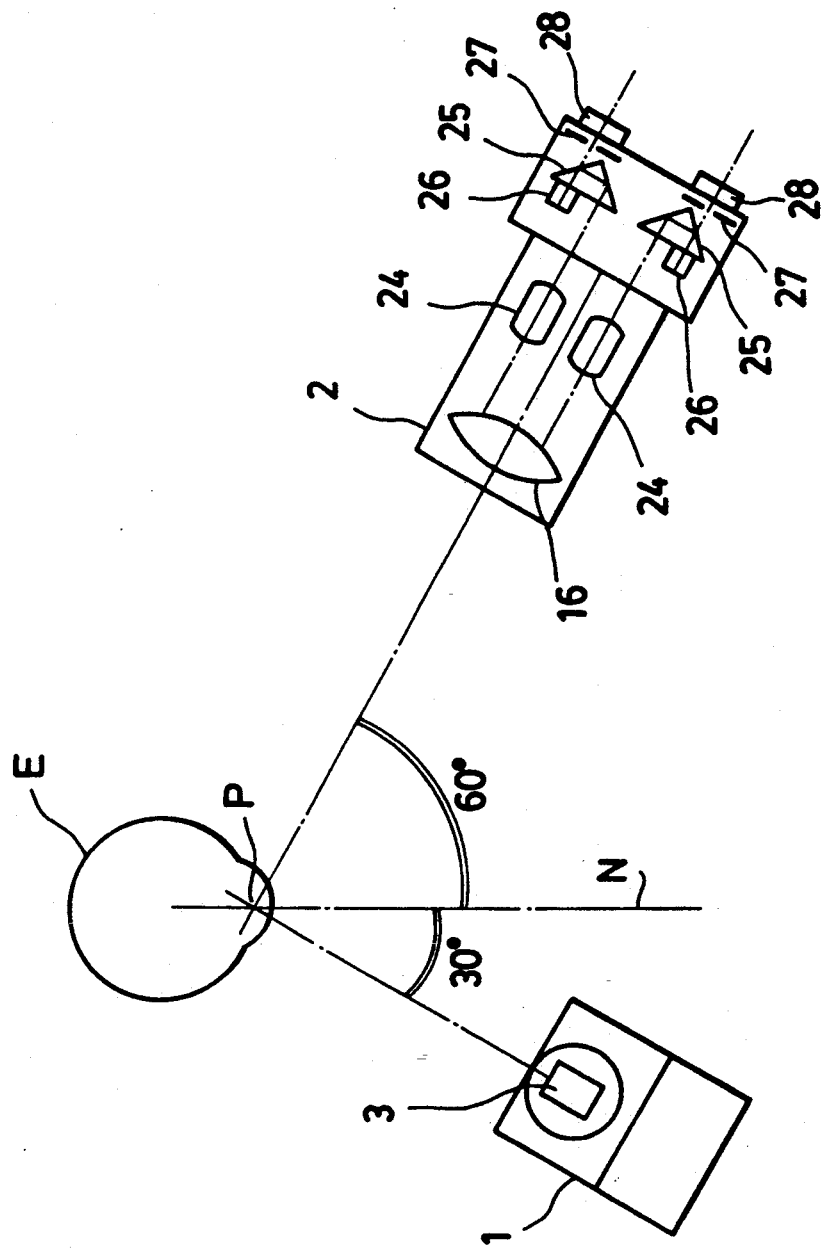
FIG. 3 shows the positional arrangement of the light projection section and the light receiving section during measurement.

FIGS. 1 to 3 show the general configuration of an embodiment of the ophthalmic measurement apparatus of this invention. In the drawings, reference numeral 1 denotes a laser light projection section in which there is a helium-neon or other such laser light source 3. The laser beam from the laser light source 3 passes through a lens 4, a movable mirror 5, a lens 6, a prism 7, a beamsplitter 9, a lens 10 and a prism 11 whereby the beam is converged on a prescribed point P in the anterior chamber of the eye E being examined.

The movable mirror 5 is connected to a mirror drive circuit 30 controlled by a computer 31 constituted by a microprocessor or the like in such a way that it allows the angle of the movable mirror 5 to be changed so as to deflect the laser beam to scan a measurement zone over a prescribed range about a center formed by a point of laser beam convergence P. As described below, this scanning range is set so that it exceeds the range of an aperture formed in a measurement mask.

The laser light projection section 1 is provided with a halogen lamp or other such white-light source 12, light from which illuminates a slit 14 via a lens 13. The light from the slit 14 thus illuminated passes via a slit light shutter 15, the beam splitter 9, the lens 10 and the prism 11 to form a slit image in the vicinity of the point of convergence P in the anterior chamber of the eye E.

By illuminating the area around the point of convergence P, the slit image allows the position of the point of convergence P to be readily confirmed when the system is being aligned. The width and length of the slit 14 can be adjusted by a slit width adjustment knob 55 and slit length adjustment knob 56 (FIG. 1) to enable the apparatus to be utilized also as a slit-lamp microscope.

The computer 31 controls the shutter 15 via a drive circuit 34 so that the shutter 15 is open during alignment and closed during measurement of protein concentration in the anterior chamber. This includes inserting the shutter 15 into, or retracting it from, the corresponding optical system by operating an input device such as a joystick 53 which is equipped with a push-button switch 54 and provided on a base 51.

Figure 6:
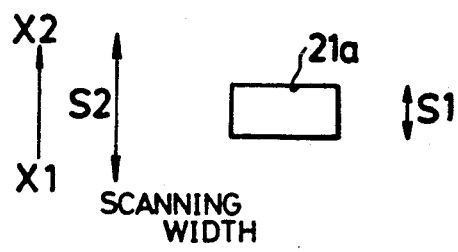

A light receiving section 2 is provided for receiving scattered light from the vicinity of the point of convergence P and to allow the area to be observed. For this, scattered light from the point of convergence P in the anterior chamber of the eye E under examination passes through a lens 16, is reflected by a semi-transparent mirror 17 and passes, via a lens 18, a photomultiplier shutter 20 and a measurement mask 21 to impinge on a photomultiplier 22 which constitutes the photosensor. Light impinging on the photomultiplier 22 is limited to light passing through an aperture 21a formed in the mask 21, which therefore serves to block extraneous light from other areas. The measurement mask 21 (aperture 21a) is provided at a position that is optically conjugate with the point of convergence P, with respect to the light receiving section 2. The aperture 21a is rectangular in shape, as can be seen in FIG. 6.

The output from the photomultiplier 22 is passed through an amplifier 23 and input to a counter 33 which counts the intensity of the scattered light detected by the photomultiplier 22 as a pulse count per unit time. These count values per unit time as counted by the counter 33 are stored at specific locations in a memory 32. The data thus stored in the memory 32 is arithmetically processed by the computer 31 to compute the protein concentration in the anterior chamber.

The shutter 20 is provided to protect the photomultiplier 22 and is open only during measurement. Like the shutter 15 it is inserted into, or retracted from, the corresponding optical system by the drive circuit 34 operated by an input device such as the joystick 53 equipped with a push-button switch 54.

Provided to the rear of the semi-transparent mirror 17 of the light receiving section is a microscope system which permits observation around the point of convergence P in the eye. With this configuration, light transmitted through the semi-transparent mirror 17 is observed by an examiner 29 via a lens 24, erect normal prisms 25 and 26, field stop 27 and eyepiece 28. As shown in FIG. 3 the microscope is provided with a double eyepiece for binocular viewing. The microscope allows the projected laser beam and the origin of undesired light rays to be observed prior to measuring the protein concentration in the anterior chamber. To enable undesired light rays to be determined as accurately as possible during system alignment, in this embodiment (as described below in further detail) the measurement zone is scanned at a higher frequency during the alignment than the frequency of the measurement scanning.

The light receiving section 2 is also provided with an alignment index 41 which is illuminated by a light-emitting diode (LED) or other such alignment light source 40. The alignment index 41 is located at a position that is conjugate with the mask 21 and with the field stop 27. Thus, the point of convergence P is conjugate with respect to the mask 21 and field stop 27, and the alignment index 41 is also conjugate with respect to the mask 21 and field stop 27. The same driver circuit 34 that drives the shutters 15 and 20 is used to control the alignment light source 40 so that it is on during alignment and off during measurement.

An eye fixation light 57 constituted, in this embodiment, by a light-emitting diode is provided at a position that permits the examiner to fix the patient's eye (FIG. 1). The eye fixation light 57 can be turned in the direction indicated by the arrow by means of a linkage 58 to enable it to be adjusted to the optimal position relative to the patient undergoing the eye examination. The light selected for the eye fixation light 57 is of a different color than the laser light.

Provided on the base 51 is an input means which in this case is the joystick 53 equipped with a push-button 54. This input means can be used for moving optical elements such as the shutters 15 and 20 into and out of the respective optical system as described above, or may be used to switch the alignment light source on and off. The laser light projection section 1 and light receiving section 2 can each rotate independently in a horizontal plane about an axis 50. With reference to FIG. 3, when the protein concentration in the anterior chamber is being measured a detent mechanism or the like is used to lock the laser light projection section 1 and the light receiving section 2 at an angle of 30 degrees and 90 degrees respectively with respect to the normal of the corneal vertex. When the apparatus is to be used as a slit-lamp microscope the two sections are unlocked to allow them to rotate freely to view the eye in cross-section.

A power supply 60 (FIG. 2) is provided which includes various components and circuitry required to provide electrical power. A lamp 61 indicates when the power supply 60 is on.

The overall operation of the apparatus thus configured will now be described. The patient's head is positioned on a chin rest, the slit light source 12 is switched on and the shutter 15 is opened to project an image of the slit 14 onto the eye E. During this alignment the shutter 20 is kept closed. The laser beam from the laser light projection section 1 is converged on the point of convergence P in the eye E and the mirror driver circuit functions to oscillate the movable mirror 5 so that the laser beam scans the measurement zone at high speed about a center formed by the point of convergence P. Here, as shown in FIG. 6, the scanning width is set to about twice the width S1 of the image of the mask aperture 21a in the eye. A high enough scanning frequency such as 50 Hz or 60 Hz is used to permit observation of the measurement zone by the human eye without any perception of flicker.

Figure 4:
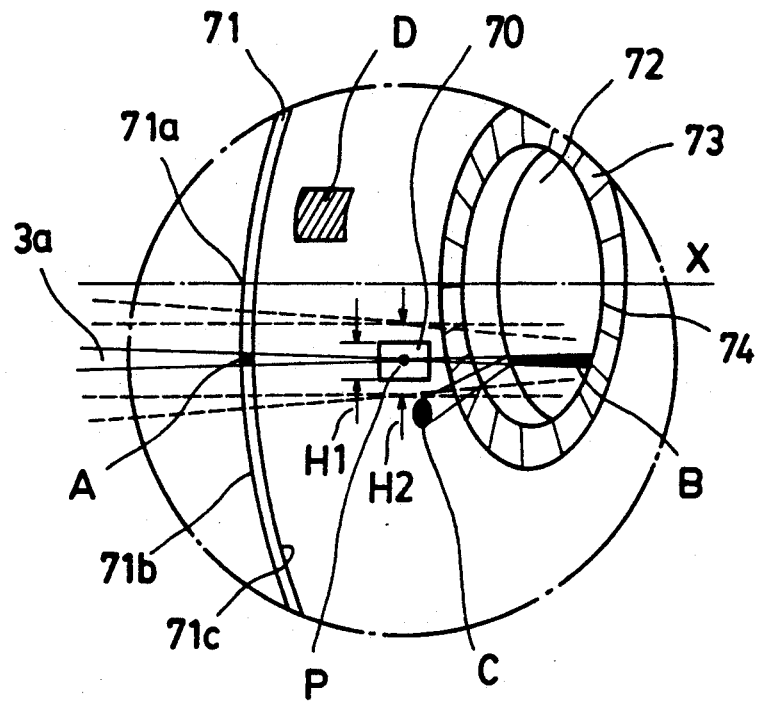
FIG. 4 is an explanatory view of the observed origin of harmful light rays.

Next, the alignment light source 40 is switched on to illuminate the alignment index 41. The image that the examiner will see at this point is shown in FIG. 4. The alignment index 41 is disposed at a position that is conjugate with the mask 21 and the field stop 27. In this case, the mask 21 and field stop 27 are conjugates of the point of convergence P and the mask 21 and field stop 27 are conjugates of the alignment index 41. As a result, an image of the alignment index 41 illuminated by the light source 40 is formed at the field stop 27 and mask 21 which are conjugate points with respect to the alignment index 41. In addition, as the field stop 27 and the mask 21 are each conjugate with respect to the point of convergence P, to the examiner 29 the alignment index 41 appears to be at the point of convergence P.

Figure 5:
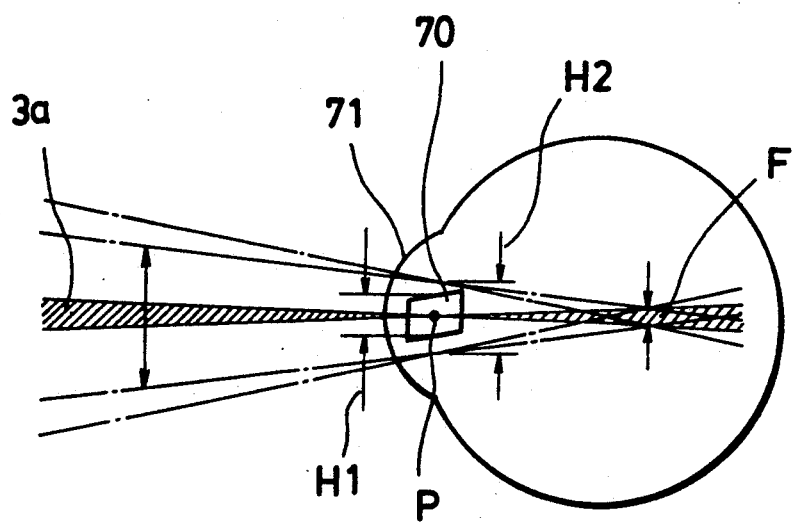
FIGS. 5 and 6 are explanatory views illustrating the range of deflection of the laser beam.

When an arrangement is used in which the size and shape of the alignment index 41 is such that the image of the alignment index on the mask 21 coincides with the aperture 21a, to the examiner it will appear that the aperture 21a is at the point of convergence P. In FIGS. 4 and 5 this image of the rectangular aperture 21a is denoted by the reference numeral 70. With reference to FIG. 4 which shows what is actually observed via the eyepiece 28, the aperture image 70 is shown more or less in the middle of the field of vision slightly below the center line X that passes through the corneal vertex 71a. To simplify the explanation, in FIG. 5 the center of the aperture image 70 is shown as coinciding with the vertex of the cornea 71.

In this embodiment the movable mirror 5 deflects the laser beam 3a over a range that is about twice the width of the image 70 of the aperture 21a. In the drawings (FIGS. 4 and 5) in which H2 is the range of a measurement zone scan sweep by the laser beam 3a and H1 is the length of the aperture image 70 measured along a short side, H2 is about twice H1. In FIG. 5, F is a point at which there is no movement even during deflection of the laser beam 3a. There is no movement at F because it is conjugate with respect to the axis of oscillation of the reflecting surface of the movable mirror 5, and therefore the oscillation of the movable mirror 5 has no bearing on it.

With reference to FIG. 4, light originating in an area outside the aperture image 70 will be unable to pass through the mask 21, so by suitably aligning the system undesired rays of light from sources such as the cornea and the crystalline lens can be directed outside the area of the mask aperture image 70, blocking the undesired light rays. Light rays which are undesired and harmful to the measurement are described below.

Light from the laser beam 3a impinging on the cornea 71 before reaching the point of convergence P is scattered from the part of the cornea 71 marked A. Although slit and laser light is actually scattered from two points, the front surface 71b and rear surface 71c of the cornea 71, because of the closeness of the two in the drawing they are shown as a single point A. The laser beam 3a passing through the point of convergence P and into the crystalline lens 72 produces scattered light B. Light reflected by the surface of the crystalline lens 72 forms an image C on the cornea 71. This harmful light B and C is particularly intense when the crystalline lens is synthetic. In FIG. 4, reference numeral 73 denotes the iris. The boundary between the iris 73 and the crystalline lens 72 forms the pupil 74. At D, a corneal image is formed by scattered light from the exit face of the prism 11. As the laser light passes through the prism 11 and converges in the eye, the laser light is scattered by the faces of the prism, producing secondary light sources that give rise to spurious images owing to the convex mirror effect of the cornea.

The above areas A to D are the main sources of undesired rays. To distinguish these undesired rays during alignment, in this embodiment, during the alignment the laser beam 3a is made to scan the measurement zone at high speed at the same scan width (H2) used for measurement scanning. Since this high-speed scanning of the measurement zone is performed at a frequency such as 50 Hz or 60 Hz that is above the flicker perception threshold of the human eye, it becomes possible to simulate the undesired light rays arising during actual measurement, which helps to distinguish and eliminate the harmful rays.

To eliminate undesired light rays A to D entails aligning the apparatus so that the rays do not come within the aperture image 70. These undesired light rays behave like scattered light sources with low directionality and illuminate the vicinity. In order to ensure that only scattered light from proteins in the anterior chamber is received, the system should by aligned to achieve a maximum separation of the undesired light sources to optimize measurement precision. Also, if the light that illuminates the alignment index is made a different color from the laser light, the mask aperture image 70 can be readily distinguished from the undesired light ray sources A to D.

Preferably the aperture image 70 in the eye should have a width that is about one-thirtieth to one-fifteenth the diameter of the dilated pupil and a length that is one-eighth to one-quarter the depth of the anterior chamber of the eye. After the above alignment is accomplished, the system mode is changed to measurement. In measurement mode, pressing the switch 54 of the joystick 53 turns off the alignment light source 40, closes shutter 15 and opens shutter 20 to enable scattered laser light to be received by the light receiving section 2 and to be measured to determine the protein concentration in the anterior chamber.

During the measurement process, the projection section 1 projects the beam of laser light at the point of convergence P of the eye E under examination and light scattering from the area around the point of convergence P is received by the photomultiplier 22 of the light receiving section 2. The movable mirror 5 is oscillated by the mirror drive circuit 30 in the direction shown by the arrow to scan the measurement zone with point P at the center. As there is no need to eliminate flicker during measurement scanning, the laser beam 3a is deflected at a lower frequency setting of about 2 Hz. The width of the scanning is set to about twice the width S1 of the aperture 21a, the same as the alignment scanning setting (FIG. 6). The photomultiplier 22 receives incident laser light via the aperture 21a and detects the intensity of the scattered light scattered by protein particles in the anterior chamber measurement zone. The scattered light intensity is converted to a corresponding pulse train and counted by the counter 33 as a pulse count per unit time period, and these count values per unit time are stored at specific locations in the memory 32. As described, with reference to FIG. 6, with one scan of the laser beam 3a being from x1 to x2, when n count values have been stored, FIG. 7 shows count values stored in the memory 32 arranged as a time series.

Figure 7:
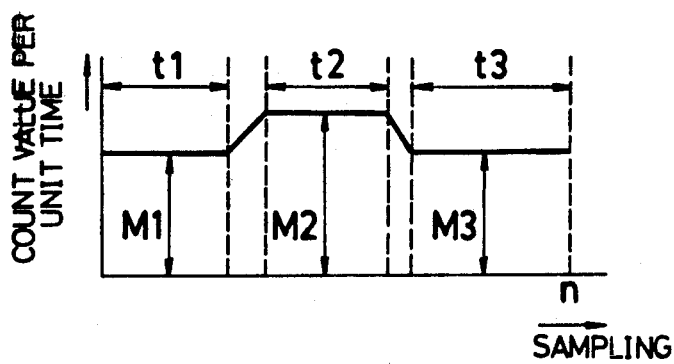
FIG. 7 is a waveform of a signal obtained from one sweep of the scanning laser beam.

With reference to FIG. 7, t1 and t3 are intervals when the incident laser beam is not within the aperture 21a and indicate the inclusion of noise components produced by intra-ocular light reflections or scattering, or the ambient brightness of the measurement environment. M1 and M3 are taken as average values of counts in the memory 32 for intervals t1 and t3. Also included as noise in M1 and M3 is the dark current of the photomultiplier 27. These noise components fluctuate from measurement to measurement.

Interval t2 is an interval during which the scattered laser light enters via the aperture 21a and includes signal components corresponding to the protein concentration in the anterior chamber, and noise components of light reflected and scattered by floating cells and from the ambient brightness. M2 is the average of the count values stored in the memory 32 during this interval.

Figure 8B:
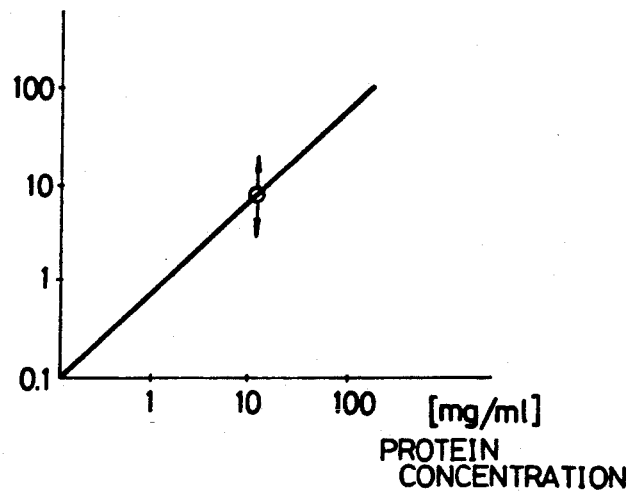
FIGS. 8a and 8b are characteristic curves plotted from obtained data values of differences in scanning widths.
Figure 8A:
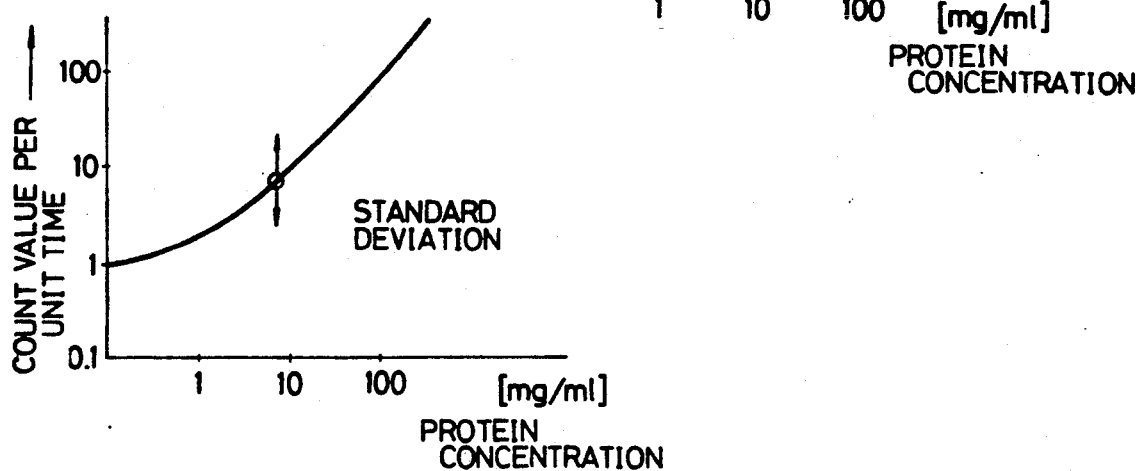

The computer 31 deducts the mean value of M1 and M3 from the value M2 stored in the memory 32 to extract the effective component for computing the protein concentration in the anterior chamber. If the system has been properly aligned, the values of M1 and M3 will be about the same. If the data were only obtained by measurement during the interval t2 the signal/noise ratio would be poor and the variance large with a corresponding degradation in reproducibility (FIG. 8a) but, as shown by FIG. 8b, in accordance with this invention the signal/noise ratio is improved by deducting the noise component, which also increases the dynamic range and improves the reproducibility.

Thus, in accordance with the present invention, high-speed laser beam scanning of the measurement zone is implemented during alignment using a scanning width that is the same as the scanning width used for the measurement. This makes it possible to observe any undesired light rays that will actually appear during measurement at those settings. Such an arrangement enables the apparatus to be aligned so that the undesired light rays do not come within the measurement mask aperture, thereby enabling measurement to be conducted under optimum conditions.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmic measurement apparatus in which a laser beam is projected at a selected point in a measurement zone within an eye to be examined and light scattered therefrom is photoelectrically detected for ophthalmic measurement, comprising:

a laser source for producing a laser beam;

projecting means for projecting the laser beam to converge it to the point in the measurement zone;

a light receiving section provided with a photosensor for photoelectrically detecting scattered laser light from the measurement zone via a measurement mask having an aperture of a prescribed size and positioned conjugate with the point of convergence of the laser beam;

deflecting means for deflecting the laser beam in a prescribed direction for scanning the area of the measurement zone during alignment of the eye and during measurement;

processing means for processing signals received from the light receiving section to perform the ophthalmic measurement; and arranging means for arranging an alignment index at a position that is conjugate with the measurement mask so that during alignment an image of the alignment index appears superimposed on an image of the measurement zone formed at the aperture of the measurement mask;

wherein during alignment the measurement zone is scanned at high speed by the laser beam having the same scanning width as the scanning width used during measurement.

2. An ophthalmic measurement apparatus according to claim 1; wherein the deflecting means includes means for high-speed scanning of the measurement zone by the laser beam at a frequency that is high enough to prevent a flicker effect when the measurement is observed by the human eye.

3. An ophthalmic measurement apparatus according to claim 1; wherein the deflecting means includes means for scanning of the measurement zone wherein the scanning of the measurement zone exceeds the size of the aperture.

4. An ophthalmic measurement apparatus according to claim 1; wherein the aperture is rectangular in shape.

5. An ophthalmic measurement apparatus according to claim 1; wherein the projecting means and the light receiving section are arranged substantially at right angles to each other.

6. An ophthalmic measurement apparatus according to claim 1; wherein the scanning width of the measurement zone is about twice the width of the rectangular aperture image in the eye.

7. An ophthalmic measurement apparatus according to claim 1; wherein the rectangular aperture image in the eye has a longitudinal length that is about one-thirtieth to one-fifteenth the diameter of the dilated pupil of the eye and a lateral length that is about one-eighth to one-quarter the depth of the anterior chamber of the eye.

8. An ophthalmic measurement apparatus according to claim 1; wherein the alignment index is illuminated by a light source which provides light of a different color from that of the laser light.

9. An ophthalmic measurement apparatus according to claim 1; wherein the alignment index is an aperture of a prescribed size and the image of this aperture on the measurement mask coincides with the aperture of the measurement mask.

10. An ophthalmic measurement apparatus in which a laser beam is projected at a selected point in a measurement zone within an eye to be examined and light scattered therefrom is photoelectrically detected for ophthalmic measurement, comprising: means for converging the laser beam to the selected point in the measurement zone; receiving means for detecting the scattered light via a measurement mask having an aperture and disposed at a position that is conjugate with the selected point; deflecting means for deflecting the laser beam for scanning an area of the measurement zone during alignment of the eye and during measurement, the deflecting means including means for scanning the measurement zone during alignment of the eye at high speed and having a same scanning width as a scanning width used during measurement; and means for arranging an alignment index at a position that is conjugate with the measurement mask so that an image of the alignment index appears superimposed on an image of the measurement zone formed at the aperture of the measurement mask during alignment of the eye.

11. An ophthalmic measurement apparatus according to claim 10; wherein the deflecting means includes means for scanning the measurement zone at a frequency effective to prevent a flicker effect when the measurement zone is observed by a human eye.

12. An ophthalmic measurement apparatus according the claim 10; wherein the scanning width is larger than the aperture.

13. An ophthalmic measurement apparatus according to claim 10; wherein the scanning width is substantially twice the width of the aperture.

14. An ophthalmic measurement apparatus according to claim 10; further comprising means for illuminating the alignment index by a light having a different color than the projected laser beam.

15. An ophthalmic measurement apparatus according to claim 10; wherein the alignment index comprises an aperture having a prescribed size, and an image of the alignment index aperture on the measurement mask coincides with the aperture of the measurement mask.

* * * * *